US008716336B2

(12) United States Patent  
Ansmann et al.

(10) Patent No.: US 8,716,336 B2
(45) Date of Patent: May 6, 2014

(54) SMOOTH-FEELING WAX-BASED COMPOSITIONS FOR PERSONAL CARE PREPARATIONS

(75) Inventors: Achim Ansmann, Erkrath (DE); Ulrich Issberner, Rommerskirchen (DE); Stefan Bruening, Duesseldorf (DE); Bettina Jackwerth, Langenfeld (DE); Daniele Hoffmann, Duesseldorf (FR)

(73) Assignee: Cognis IP Management GmbH, Duesseldorf (DE)

( * ) Notice: Subject to any disclaimer, the term of this patent is extended or adjusted under 35 U.S.C. 154(b) by 275 days.

(21) Appl. No.: 12/051,229

(22) Filed: Mar. 19, 2008

(65) Prior Publication Data
US 2008/0166431 A1 Jul. 10, 2008

Related U.S. Application Data

(63) Continuation of application No. 10/483,534, filed as application No. PCT/EP02/07787 on Jul. 12, 2002, now abandoned.

(30) Foreign Application Priority Data

Jul. 13, 2001 (DE) .................................. 101 33 399

(51) Int. Cl.
*A61K 31/265* (2006.01)
*A61K 8/00* (2006.01)
*A61K 8/02* (2006.01)
*A61K 8/18* (2006.01)

(52) U.S. Cl.
USPC ................ 514/512; 424/63; 424/64; 424/401

(58) Field of Classification Search
USPC ................................ 424/401, 63, 64; 514/512
See application file for complete search history.

(56) References Cited

U.S. PATENT DOCUMENTS

| 3,269,971 | A | * | 8/1966 | Goldblum | ............ 524/280 |
| 4,202,879 | A | | 5/1980 | Shelton | |
| 5,069,897 | A | | 12/1991 | Orr | |
| 5,665,426 | A | | 9/1997 | Krzysik et al. | |
| 5,718,887 | A | | 2/1998 | Wolfe et al. | |
| 5,840,943 | A | | 11/1998 | Ansmann et al. | |
| 5,871,763 | A | * | 2/1999 | Luu et al. | .......... 424/402 |
| 6,153,204 | A | * | 11/2000 | Fanger et al. | ............ 424/401 |
| 6,207,014 | B1 | | 3/2001 | De Haut et al. | |
| 6,228,831 | B1 | * | 5/2001 | Ansmann et al. | ............ 510/416 |
| 2003/0053970 | A1 | | 3/2003 | Bruening et al. | |

FOREIGN PATENT DOCUMENTS

| DE | 33 09 530 | | 10/1984 |
| DE | 41 19 890 | | 12/1992 |
| DE | 4119890 | A1 * | 12/1992 |
| DE | 195 11 668 | | 10/1996 |
| DE | 198 31 705 | | 3/1999 |
| DE | 198 28 020 | | 12/1999 |
| DE | 199 43 585 | | 3/2001 |
| EP | 0 691 125 | | 1/1996 |
| EP | 0 766 661 | | 4/1997 |
| JP | 11-106326 | | 4/1999 |
| JP | 2000095662 | A * | 4/2000 |
| WO | WO 95/16824 | | 6/1995 |
| WO | WO 95/35411 | | 12/1995 |
| WO | WO 95 35412 | | 12/1995 |
| WO | WO 96/24723 | | 8/1996 |
| WO | WO 97/30216 | | 8/1997 |
| WO | WO 97/46205 | | 12/1997 |
| WO | WO 99/17714 | | 4/1999 |
| WO | WO 01/22933 | | 4/2001 |
| WO | WO 01/39766 | | 6/2001 |
| WO | WO 01/52806 | | 7/2001 |
| WO | WO 01/56396 | | 8/2001 |

OTHER PUBLICATIONS

Derwent abstract of DE 4119890 A1.*
Machine translation of DE 4119890 A1.*
Machine Translation of JP 2000095662 A.*
Machine Translation of JP 2000095662 A. Orginal Publication Date: Apr. 2000. Date Translated: Dec. 17, 2012.*
Derwent Abstract of DE 4119890 A1. Original Publication Date: Dec. 24, 1992.*
Machine Translation of DE4119890 A1. Original Publication Date: Dec. 24, 1992. Date Translated: Sep. 12, 2007.*
Mathis, R. E. "Paradigm Shift in Finishes for Coverstock: Active Care Instead of Hamlessness," *Nonwovens World*, 8:5, pp. 59-62 (1999).
Shaikh, A. G., et al., "Organic Carbonates," *Chem. Rev.* 96:3, pp. 951-976 (1996).

(Continued)

*Primary Examiner* — Sreeni Padmanabhan
*Assistant Examiner* — Jody Karol
(74) *Attorney, Agent, or Firm* — Servilla Whitney LLC

(57) ABSTRACT

A smooth, dry-feeling, less-greasy, substantially-odorless, ecotoxicologically-safe, wax-based composition with a melting point above 25° C., comprising one or more wax components selected from dialkyl carbonates, dialkylene carbonates, and mixtures of two or more thereof; less than 10%, by weight, of water; and (c) optionally, one or more components selected from the group consisting of one or more wax or oil components selected from the group consisting of dialkyl ethers, dialkylene ethers, dicarboxylic acids, hydroxyfatty alcohols, and mixtures of two or more thereof, as well as one or more wax-like lipid components, other than those in previously listed, one or more other oil components, liquid at 20° C. and immiscible with water at 25° C., other than those previously listed, one or more emulsifiers, one or more zwitterionic, amphoteric, cationic or anionic surfactants, one or more other auxiliaries and/or additives, and one or more physiologically-active components, which compositions are useful in a cosmetic, personal hygiene and/or body-care preparation.

6 Claims, No Drawings

(56) References Cited

OTHER PUBLICATIONS

Lipide, CD Römpp Chemie Lexikon—Version 1.0, Stuttgart/New York: Georg Thieme Verlag (1995).
Basam, M. et al., "Emollient Creams and Lotions," *Cosmetics: Science and Technology*, eds., vol. 1, pp. 27-104 (1972).
Leitfaden zur Inhaltsstoffdeklaration Kosmetischer Mittel, Industrieverband Körperpflege-und Waschmittel e.V., $3^{rd}$ Edition, pp. 44-45.
Kirk-Othmer "Encyclopedia of Chemical Technology," $3^{rd}$ Edition, vol. 8, p. 913, 1979.
"Puder," CD Römpp Chemie Lexikon—Version 1.0, Stuttgart/New York: Georg Thieme Verlag (1995).
Die Kosmetik-Verordnung, Appendix 6, parts A and B.
International Search Report PCT/EP2002/07787, Dec. 2, 2003.
English Abstract of DR 41 19 890 A1 provided by Derwent, Accession No. 1993-000537.
Machine translation of DE 41 19 890 A1.
"Jojoba: A Botanical with Proven Functionality", *Cosmetics & Toiletries*, vol. 98 1983, 81-83.
"Scientific Literature Review on Jojoba Oil", *Cosmetic Ingredient Review* 1988, 4 pgs.

* cited by examiner

SMOOTH-FEELING WAX-BASED COMPOSITIONS FOR PERSONAL CARE PREPARATIONS

CROSS-REFERENCE TO RELATED APPLICATIONS

This application is a continuing application of U.S. patent application Ser. No. 10/483,534, filed Jun. 29, 2004 now abandoned, which claimed priority under 35 U.S.C. §371 based upon International Application No. PCT/EP02/07787, having an International Filing Date of Jul. 12, 2002, the entire contents of each of which are herein incorporated by reference.

BACKGROUND OF THE INVENTION

1. Field of the Invention

This invention relates to special wax-based compositions which may be used as a basis for cosmetic preparations.

2. Background and Related Art

The generic term "paper" encompasses about 3,000 different types and articles which can differ, sometimes considerably, in their applications and their properties. Their production involves the use of numerous additives among the most important of which are fillers (for example chalk or kaolin) and binders (for example starch). For tissues and hygiene papers, which come into relatively close contact with the human skin, there is a particular need for an agreeable soft feel which is normally given to the paper by careful selection of the fibers and, in particular, by a high percentage of fresh mechanical wood pulp or cellulose. However, in the interests of economic paper manufacture and from the ecological perspective, it is desirable to use large amounts of inferior-quality deinked wastepaper. Unfortunately, this means that the softness of the paper is significantly reduced which is troublesome in practice and can even lead to irritation of the skin, particularly with frequent use of such paper products.

Accordingly, there has been no shortage of attempts in the past to treat tissue and other papers by impregnation, coating or other surface treatments in such a way that a more agreeable feeling of softness is achieved. This requires the development of special lotions and emulsions which, on the one hand, are easy to apply to the paper and, on the other hand, do not adversely affect its structure. Softness is often improved by the use of nonionic surfactants or a combination of nonionic and anionic surfactants. Polysiloxanes and cationic polymers are also used for this purpose.

International patent application WO 95/35411 relates to tissue papers coated with softening formulations which contain 20 to 80% by weight of a water-free emollient (mineral oils, fatty acid esters, fatty alcohol ethoxylates, fatty acid ethoxylates, fatty alcohols and mixtures thereof), 5 to 95% by weight of an "immobilizing agent" for the emollient (fatty alcohols, fatty acids or fatty alcohol ethoxylates containing 12 to 22 carbon atoms in the fatty component) and 1 to 50% by weight of surfactants with an HLB value of preferably 4 to 20. The Examples of this document all contain petrolatum as emollient. International patent application WO 95/35412 discloses similar tissue papers where water-free mixtures of (a) mineral oils, (b) fatty alcohols or fatty acids and (c) fatty alcohol ethoxylates are used as softeners. International patent application WO 95/16824 describes softening formulations for tissue papers containing mineral oil, fatty alcohol ethoxylates and nonionic surfactants (sorbitan esters, glucamides). In addition, International patent application WO 97/30216 (Kaysersberg) describes liquid softening formulations for paper handkerchiefs based on long-chain saturated fatty alcohols and wax esters with, in all, at least 24 carbon atoms which have a very high water content. DE 33 09 530 describes hygienic absorbent materials which are coated with glycerides and/or partial glycerides of coconut oil fatty acids. Coatings for personal hygiene products are also described by R. E. Mathis in "Nonwovens World" 1999, pages 59-65.

From the performance perspective, however, the sensory properties of the treated papers and tissues are still in need of improvement. The coatings in use at present often leave the skin feeling too greasy and, in some cases, are distinguished by an overly slow release of active ingredients. In the field of baby hygiene in particular, the effective release of active components, an improved care effect and better sensory properties are very important requirements.

The problem addressed by the present invention was to provide compositions for coating tissue papers and wet wipes which would be distinguished by improved sensory properties and, more particularly, by a less greasy feeling on the skin. In addition, the compositions would be able to be applied in liquefied form to the papers and would allow the papers to be aftertreated with water without the compositions dissolving. The compositions would also be stable in storage after application to papers/wipes subsequently treated with water and would not mix, i.e. would not form emulsions in the event of prolonged storage. The compositions to be provided by the invention would also ensure the efficient release of active components. The coated wipes would have excellent personal (skin) care properties and would be distinguished by particular mildness and dermatological compatibility. In addition, only readily biodegradable auxiliaries would be used and, despite their very low water content, the preparations would readily penetrate into the tissue, would be uniformly distributed and would be readily processable.

BRIEF SUMMARY OF THE INVENTION

The instant invention is directed to a smooth, dry-feeling, less-greasy, substantially-odorless, ecotoxicologically-safe, wax-based composition with a melting point above 25° C., preferably from 30-to 45° C., more preferably from 32-to-40° C., comprising (a) one or more wax components selected from symmetrical or unsymmetrical, linear or branched, saturated or unsaturated dialkyl carbonates, preferably $C_{14}$-$C_{30}$-, more preferably $C_{16}$-$C_{24}$-, most preferably $C_{16}$-$C_{22}$-dialkyl carbonates, symmetrical or unsymmetrical, linear or branched, saturated or unsaturated dialkylene carbonates, preferably $C_{14}$-$C_{30}$-, more preferably $C_{16}$-$C_{24}$-, most preferably $C_{16}$-$C_{22}$-dialkylene carbonates, and mixtures of two or more thereof, (b) less than 10%, preferably less than 6%, more preferably less than 3%, by weight, of water, and most preferably water-free, except for small amounts of water originating with the raw materials of the composition; and (c) optionally, one or more components selected from the group consisting of (i) one or more wax or oil components selected from the group consisting of symmetrical or unsymmetrical, branched or unbranched, saturated or unsaturated dialkyl ethers, preferably $C_{16}$-$C_{30}$-, more preferably $C_{16}$-$C_{24}$-, most preferably $C_{16}$-$C_{20}$-dialkyl ethers, symmetrical or unsymmetrical, branched or unbranched, saturated or unsaturated dialkylene ethers, preferably $C_{16}$-$C_{30}$-, more preferably $C_{16}$-$C_{24}$-, most preferably $C_{16}$-$C_{20}$-dialkylene ethers, dicarboxylic acids, preferably $C_9$-$C_{34}$-, more preferably $C_9$-dicarboxylic acids, saturated or unsaturated, branched or unbranched hydroxyfatty alcohols, preferably $C_{12}$-$C_{30}$-hydroxyfatty alcohols, and mixtures of two or more thereof, (ii) one or more wax-like lipid components, other than those in (a) or (i), such as fats, such as triacylglycerols, and fat-like substances, particularly fatty alcohols, preferably $C_{15}$-$C_{50}$-, more preferably $C_{12}$-$C_{24}$-fatty alcohols or one or more fatty acid glycerides, (iii) one or more other oil components, liquid at 20° C. and immiscible with water at 25° C., other than those in (a) or (i), such as glycerides, hydrocarbons, ester oils, one or more silicone compounds selected from the group consisting of silicone oils and silicone waxes, and the like (iv) one or more emulsifiers, (v) one or more zwitterionic, amphoteric, cationic or anionic surfactants, (vi) one or more other auxiliaries and/or additives, such as powders, oil-soluble dyes, moisturizers, and the like, and (ix) one or more physiologically-active components, which compositions are useful in a cosmetic, personal hygiene and/or body-care preparation, and may be applied, in a liquefied form, to papers, wipes, sponges, tissues, plasters, puffs, bandages, and the like for such purposes, without the composition dissolving if the substrate is aftertreated with aqueous/surfactant-containing solutions.

DETAILED DESCRIPTION OF THE INVENTION

It has been found that wax-like preparations containing special oil or wax components and very little water have excellent sensory and care properties, are very easy to apply and are distinguished by particular mildness.

Accordingly, the present invention relates to wax-based compositions with a melting point above 25° C. containing
(a) at least one oil or wax component selected from dialkyl (ene) ethers, dialkyl(ene) carbonates, dicarboxylic acids or hydroxyfatty alcohols or a mixture of these substances,
(b) less than 10% by weight water.

Waxes are normally understood to be natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. Wax-like compositions distinguished by a melting point above 25° C. may be used in accordance with the invention.

The presence of special oil or wax components selected from dialkyl(ene) ethers, dialkyl(ene) carbonates, dicarboxylic acids or hydroxyfatty alcohols or mixtures thereof enables the sensory properties in particular of the wax-like compositions to be optimized so that they feel less greasy and, instead, have a dry feeling on the skin, but still show excellent care properties. The compositions according to the invention contain less than 10% by weight water, preferably less than 6% by weight water and more particularly less than 3% by weight water. In a particularly preferred embodiment, the compositions are water-free. Water-free in the context of the invention means that the compositions may have a small water content originating from their raw materials, but do not contain any added water. In the processing and application of the composition to the wipes, the wipes can thus be aftertreated with aqueous/surfactant-containing solutions without the composition dissolving.

The compositions according to the invention may be formulated exclusively from dialkyl(ene) ethers, dialkyl(ene) carbonates, dicarboxylic acids, hydroxyfatty alcohols and/or mixtures thereof with a wax-like consistency, but preferably contain other wax-like lipid components and oils according to the requirement profile. The melting range of the composition as a whole must be above 25° C., i.e. the composition can be applied to the papers in liquefied form above that temperature. Accordingly, liquid dialkyl(ene) ethers, dialkyl(ene) carbonates, dicarboxylic acids or hydroxyfatty alcohols may also be used in accordance with the invention providing the composition as a whole has the required melting point of higher than 25° C. A preferred embodiment is characterized in that the composition melts in the range from ca. 30 to 45° C. and more particularly in the range from 32 to 40° C. This ensures that, after coating of the paper, the composition resolidifies so that the wipes can be aftertreated with aqueous/surfactant-containing solutions and/or lotions and a soft nonbrittle film is left behind on the wipes. Wipes coated with such compositions are particularly stable in storage and mixing of the phases is avoided. In addition, the composition only melts again when the wipes are applied to the skin and only then is it emulsified with the aqueous phase.

According to the invention, compositions with a penetration value of 0.2 to 3.0 mm (apparatus: Petrotester PNR 10, microcone, 5 secs., temperature 20° C.) are particularly advantageous.

The dialkyl(ene) ethers may be symmetrical or nonsymmetrical, branched or unbranched, saturated or unsaturated. Dialkyl(ene) ethers particularly suitable for the purposes of the invention are wax-like saturated $C_{16-30}$ dialkyl ethers, more particularly $C_{16-24}$ dialkyl ethers. $C_{16-20}$ dialkyl ethers are particularly preferred, distearyl ether and dibehenyl ether being most particularly suitable. Relatively short-chain dialkyl ethers, for example di-n-octyl ether, di(2-ethylhexyl) ether, lauryl methyl ether or octyl butyl ether, didocecyl ether, may also be used in accordance with the invention providing the composition as a whole has the required melting point. The compounds can be produced from fatty alcohols in the presence of acidic catalysts by generally known methods, cf. for example DE 195 11 668 A1, DE 198 31 705 A1 and DE 199 43 585. Typical examples of such ethers are products obtained by etherification of caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachidyl alcohol, gadoleyl alcohol, behenyl alcohol, erucyl alcohol and brassidyl alcohol, Guerbet alcohols and the technical mixtures thereof obtained for example in the high-pressure hydrogenation of technical methylesters based on fats and oils. Dialkyl(ene) ethers solid at 25° C. are particularly suitable.

The dialkyl(ene) carbonates may be symmetrical or non-symmetrical, branched or unbranched, saturated or unsaturated. Among the dialkyl carbonates, wax-like, linear or branched, saturated or unsaturated $C_{14-30}$ dialkyl(ene) carbonates are preferred for the purposes of the invention. $C_{16-24}$ dialkyl(ene) carbonates are particularly preferred and, of these, saturated unbranched $C_{16-22}$ dialkyl carbonates are particularly suitable. Distearyl carbonate is most particularly preferred. However, liquid dialkyl(ene) carbonates such as, for example, dihexyl, dioctyl, di-(2-ethylhexyl) or dioleyl carbonate may also be used in accordance with the invention providing the composition as a whole has the required melting point. The compounds may be obtained by transesterification of dimethyl or diethyl carbonate with the corresponding hydroxy compounds by known methods. A relevant overview can be found in "Chem. Rev." 96, 951 (1996).

Typical examples of dialkyl(ene) carbonates are transesterification products of dimethyl and/or diethyl carbonate with caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachidyl alcohol, gadolelyl alcohol, behenyl alcohol, erucyl alcohol and brassidyl alcohol, Guerbet alcohols and the technical mixtures thereof obtained, for example, in the high-pressure hydrogenation of technical methyl esters based on fats and oils. Dialkyl(ene) carbonates solid are 25° C. are particularly suitable.

According to the invention, $C_{9-34}$ dicarboxylic acids may be used as the dicarboxylic acids. Such acids include, for example, octadecanedioic acid, tetramidecanoic acid, etc. According to the invention, azelaic acid—a $C_9$ dicarboxylic acid—is particularly suitable.

Among the hydroxyfatty alcohols, saturated or unsaturated, branched or unbranched alcohols are suitable. $C_{12-30}$ fatty alcohols are preferred, the position of the hydroxy substituent being dependent upon the synthesis route and the educts used. Such fatty alcohols include, for example, decane-1,10-diol (Speziol® 10/2), hexanedecane-1,2-diol, 12-hydroxystearyl alcohol or hydroxyguerbet alcohols. According to the invention, hydroxyfatty alcohols solid at 25° C. are particularly suitable although liquid hydroxyfatty alcohols may also be used providing the composition as a whole has the required melting point. The 12-hydroxystearyl alcohol marketed by Cognis France S.A. under the name of Speziol® 18/2 is particularly preferred. Hexanecane-1,2-diol is obtained by ring opening of the corresponding α-epoxide.

The dialkyl ethers, dialkyl carbonates and dicarboxylic acids and hydroxyalcohols are present in a total quantity of preferably 1 to 30% by weight, more preferably 1 to 20% by weight and most preferably 1 to 10% by weight, based on the composition as a whole.

The compositions according to the invention are substantially odorless, ecotoxicologically safe and readily biodegradable. They are suitable as fat-containing, mild cosmetic preparations and may also be incorporated as a base in cosmetic personal hygiene and body care preparations, such as creams, lotions, sprayable emulsions, sun protection products, antiperspirants, liquid and bar soaps. etc. They may be applied as a personal care component to tissues, papers, wipes, sponges, puffs, plasters and bandages which are used in the field of hygiene and care (wet wipes for baby hygiene and baby care, cleaning wipes, facial wipes, skin care wipes, wipes containing active components against skin ageing, wipes containing sun protection formulations and insect repellents and wipes for makeup or for aftersun treatment, wet toilet wipes, and antiperspirant wipes).

Through the incorporation of other auxiliaries and additives, the compositions according to the invention may be marketed as powders, tablets, in porous form, as granules, in encapsulated or microencapsulated form.

Other Wax-Like Lipid Components

In another preferred embodiment, the composition contains other wax-like lipid components. Through the addition of other wax-like lipid components, the sensory properties and the stability of the composition after application to papers can be further optimized and adapted to the requirement profile.

According to the invention, any fats and fat-like substances with a wax-like consistency may be used as other lipid components (for a definition, see CD Römpp Chemie Lexikon—Version 1.0, Stuttgart/New York: Georg Thieme Verlag 1995). These include inter alia fats (triglycerides), mono and diglycerides, waxes, fatty and wax alcohols, fatty acids, esters of fatty alcohols and fatty acid amides or mixtures of these substances. They may be present in the compositions according to the invention in a total quantity of 0.1 to 90% by weight, preferably 5 to 65% by weight and more particularly 20 to 65% by weight.

Fats

Fats in the context of the invention are understood to be triacylglycerols, i.e. the triple esters of fatty acids with glycerol. Among the triacylglycerols, those which melt at 30 to 45° C. and more particularly at 32 to 40° C., i.e. which have a melting range comparable with that of the composition as a whole, are preferred as the lipid component. They preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina® HR. Gycerol tristearate, glycerol tribehenate (for example Syncrowax® HRC), glycerol tripalmitate or the triglyceride mixtures known under the name of Syncrowax® HGLC, are also suitable providing the melting point of the composition as a whole is above 25° C. and preferably in the range from 30 to 45° C.

Besides the triglycerides, other suitable lipid components are mono- and diglycerides and mixtures of glycerides. According to the invention, preferred glyceride mixtures include the products Novata® AB and Novata® B (mixture of $C_{12-18}$ mono-, di- and triglycerides) and Cutina® MD or Cutina® GMS (glyceryl stearate) marketed by Cognis GmbH. A preferred embodiment of the composition according to the invention contains at least one fatty acid glyceride from the group of mono-, di- or triesters of glycerol with fatty acids or a mixture thereof as another wax-like lipid component. The glyceride (mixture) is present in a quantity of normally less than 80% by weight, preferably less than 70% by weight and more particularly less than 60% by weight, based on the weight of the composition as a whole.

Mixed esters and mixtures of mono-, di- and triglycerides are particularly suitable for the purposes of the invention because they have a relatively low tendency towards crystallization and thus improve the performance of the composition according to the invention.

Fatty Alcohols and Fatty Acids

Fatty alcohols suitable for use in accordance with the invention include $C_{12-50}$ fatty alcohols, more particularly $C_{12-24}$ fatty alcohols obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol and Guerbet alcohols. According to the invention, saturated, branched or unbranched alcohols are preferred. However, unsaturated, branched or unbranched fatty alcohols may also be used for the purposes of the invention providing the composition as a whole has the required melting point. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols®) or the partly branched alcohols from the oxosynthesis (Dobanols®) may also be used.

A preferred embodiment of the composition according to the invention contains at least one fatty alcohol as another wax-like lipid component. $C_{14-18}$ fatty alcohols marketed for example by Cognis GmbH under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are particularly suitable for the purposes of the invention. The $C_{16/18}$ Guerbet alcohol marketed by Cognis GmbH under the name of Eutanol® G32/26 is also particularly suitable. Fatty alcohols give the compositions a dryer feeling on the skin than triglycerides and are therefore preferably used.

$C_{14-40}$ fatty acids or mixtures thereof may be used as additional wax-like lipid components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes

Waxes suitable for use in accordance with the present invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat.

According to the invention, it may be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The wax component may also be selected from the group of esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of longchain hydroxycarboxylic acids. Wax components such as these include, for example, $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. Other suitable wax components which may be used with advantage are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate. Myristyl lactate (Cegesoft® C17) inter alia is particularly suitable for skin-care wipes because it binds well to the skin. Silicone waxes may also be used with advantage.

Small quantities of alkali metal and alkaline earth metal and aluminium salts of $C_{12-24}$ fatty acids or $C_{12-24}$ hydroxyfatty acids may optionally be used as additional consistency factors, calcium, magnesium, aluminium and, in particular, zinc stearate being preferred.

Oil Components

In another preferred embodiment, the composition according to the invention contains at least one oil component. In the context of the invention, oil components are substances or mixtures of substances which are liquid at 20° C. and immiscible with water at 25° C. Such substances include any oil components which are not among the dialkyl(ene) ethers, dialkyl(ene) carbonates, dicarboxylic acids or hydroxyfatty alcohols mentioned above, i.e. for example glycerides, hydrocarbons, silicone oils, ester oils liquid at 20° C. or mixtures thereof. The oil components are present in the compositions according to the invention is quantities of normally less than 40% by weight, preferably 1 to 15% by weight and more particularly 2 to 10% by weight, based on the composition as a whole. The quantity of oils incorporated is limited by the proviso that the melting point of the composition as a whole must be above 25° C. Such optimizations are among the routine optimizations of the practitioner.

Glycerides suitable as oil components in accordance with the invention include fatty acid esters of glycerol liquid at 20° C. which may be of natural (animal and vegetable) or synthetic origin. Glycerides are divided into mono-, di- and triglycerides. They are known substances which may be obtained by the relevant methods of preparative organic chemistry. Synthetic glycerides are normally mixtures of mono, di and triglycerides which are obtained by transesterification of the corresponding triglycerides with glycerol or by selective esterification of fatty acids. Preferred fatty acids for the purposes of the invention are $C_{6-24}$ fatty acids and, among these, $C_{6-18}$ fatty acids and especially $C_{8-18}$ fatty acids. The fatty acids may be branched or unbranched, saturated or unsaturated. According to the invention, it is preferred to use glycerides of vegetable origin liquid at 20° C., more particularly cocoglycerides, a mixture of predominantly di- and triglycerides with $C_{8-18}$ fatty acids marketed under the name of Myritol® 331 by Cognis Gmb H. It is also preferred to use Myritol® 312 ($C_{8/10}$ triglycerides), Cegesoft® PS 17, Cegesoft® GPO, Cegesoft® PFO and Cegesoft® PS 6 which give the compositions particularly favorable care properties after application.

Other suitable oil components are Guerbet alcohols liquid at 20° C. based on fatty alcohols containing 6 to 18 and preferably 8 to 10 carbon atoms, such as Eutanol® G for example. Liquid esters of linear, saturated or unsaturated $C_{6-22}$ fatty acids with linear or branched, saturated or unsaturated $C_{6-22}$ fatty alcohols or esters of branched $C_{6-13}$ carboxylic acids with linear or branched, saturated or unsaturated $C_{6-22}$ fatty alcohols, such as Cetiol® CC for example, may also be used as oil components in accordance with the invention.

Examples of wax esters include the following typical representatives: decyl oleate (Cetiol® V), cococaprylate/caprate (Cetiol® SN), hexyl laurate (Cetiol® A), myristyl myristate (Cetiol® MM), myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate (Cetiol® DAB), oleyl behenate, oleyl erucate (Cetiol® J 600), behenyl isostearate, behenyl oleate, erucyl isostearate, erucyl oleate. Also suitable are esters of linear $C_{6-22}$ fatty acids with branched alcohols, more particularly 2-ethyl hexanol (Cetiol® 868), esters of branched $C_{6-22}$ fatty acids with linear alcohols, esters of $C_{18-}$ alkylhydroxycarboxylic acids with linear or branched $C_{6-22}$ fatty alcohols, esters of linear and/or branched fatty acids with polyhydric alcohols (for example propylene glycol, dimer diol or trimer triol) and/or Guerbet alcohols and esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms (for example, dioctyl malate) or polyols containing 2 to 10 carbon atoms and 2 to 6 hydroxyl groups.

Other oil components suitable for use in accordance with the invention are natural and synthetic, aliphatic and/or naphthenic hydrocarbons liquid at 20° C., such as for example squalane, squalene, paraffin oils, isohexadecane, isoeicosane or polydecenes and dialkyl cyclohexanes (Cetiol®).

According to the invention, other suitable oil components are liquid silicone oils. These include, for example, dialkyl and alkylaryl siloxanes, such as for example cyclomethicone, dimethyl polysiloxane and methylphenyl polysiloxane and alkoxylated and quaternized analogs thereof. Suitable non-volatile silicone oils, such as for example polyalkyl siloxanes, polyalkylaryl siloxanes and polyether siloxane copolymers are described in Cosmetics: Science and Technology, eds.: M. Balsam and E. Sagarin, Vol. 1, 1972, pp. 27-104, in U.S. Pat. No. 4,202,879 and U.S. Pat. No. 5,069,897. A preferred embodiment of the composition according to the invention additionally contains at least one silicone compound selected from the group of silicone oils or silicone waxes. The addition of silicone compounds imparts a particularly light feeling on the skin.

Active Components

A preferred embodiment of the composition according to the invention additionally contains at least one active component. According to the invention, the active components may be used in encapsulated or microencapsulated form.

In the context of the invention, active components are understood to be substances which contribute towards protecting the skin and strengthening the skin barrier and have an irritation-soothing, antimicrobial or skin-moisturizing effect. Preferred active components according to the invention are those which soothe inflammatory skin processes or reddened, sore skin, including for example zinc compounds and sulfur. The active component is present in a quantity of normally 0.01 to 10% by weight, preferably 0.1 to 7% by weight and more particularly 1 to 5% by weight, according to the type of compound chosen. Oil-soluble active components are preferred for the purposes of the invention although limited quantities of water-soluble active components may also be incorporated through the addition of emulsifiers and/or solubilizers. The active components may also be present in combination with one another.

Also suitable are plant extracts which often contain a synergistic combination of wound-healing/irritation-soothing substances. These extracts are normally obtained by extraction of the whole plant. In individual cases, however, it can also be preferred to prepare the extracts exclusively from flowers and/or leaves of the plant.

So far as the plant extracts suitable for use in accordance with the invention are concerned, reference is made in particular to the extracts listed in the Table beginning on page 44 of the of the 3rd Edition of the Leitfaden zur Inhaltsstoffdeklaration kosmetischer Mittel, published by the Industrieverband Körperpflege- und Waschmittel e.V. (IKW), Frankfurt.

According to the invention, the extracts of, above all, chamomile, aloe vera, hamamelis, lime blossom, horse chestnut, green tea, oak bark, stinging nettle, hops, burdock root, horse willow, hawthorn, almond, pine needle, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root are suitable.

Suitable extractants for the preparation of the plant extracts mentioned are water, alcohols and mixtures thereof. Among the alcohols, lower alcohols, such as ethanol and isopropanol, but especially polyhydric alcohols, such as ethylene glycol and propylene glycol, are preferably used both as sole extractant and in the form of mixtures with water. Plant extracts based on water/propylene glycol in a ratio of 1:10 to 10:1 have proved to be particularly suitable.

Antimicrobial/Biogenic Active Components

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenylbiguanido)-hexane) or TCC (3,4,4'-trichlorocarbanilide). Numerous perfumes and essential oils also have antimicrobial properties. Typical examples are the active substances eugenol, menthol and thymol in nettle, mint and thyme oil. Interesting natural deodorants are the terpene alcohol farnesol (3,7,11-trimethyl-2,6,10-dodecatrien-1-ol) which is present in lime blossom oil and which smells of lily-of-the-valley and chitosan which is obtained from the shells of crustaceans. Glycerol monolaurate, glycerol stearate, glycerol oleate and glycerol diolate have also been found to show germ-inhibiting activity and, by virtue of their particular mildness and harmlessness, may be used with particular advantage in baby hygiene and baby care. In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, α-hydroxycarboxylic acids, amino acids, ceramides, pseudoceramides, essential oils, plant extracts and vitamin complexes. According to the invention, preferred active components are oil-soluble vitamins and vitamin precursors. Tocopherol (vitamin E) and tocopherol derivatives are most particularly preferred.

According to the invention, other suitable active components are the compounds marketed under the name of Generol®, including ethoxylated and non-ethoxylated phytosterols.

The percentage content of germ inhibitors is normally about 0.1 to 2% by weight, based on the composition as a whole. The glycerol esters may be used in relatively large quantities (vide supra).

Humectants/Skin Moisturizers

In a preferred embodiment, the composition according to the invention also contains a humectant as an active component. This active component contributes towards improving the sensory properties of the composition and serves to regulate the skin moisture level. In addition, ft can contribute towards improving the penetration behavior of the composition on the wipes. The humectants are normally present in a quantity of 0.1 to 20% by weight, preferably 1 to 15% by weight and more particularly 5 to 10% by weight.

According to the invention, suitable humectants are inter alia amino acids, pyrrolidone carboxylic acid, lactic acid and salts thereof lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof, ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol and triglycerol.

Emulsifiers

Another preferred embodiment of the composition according to the invention additionally contains at least one emulsifier. Small quantities of water-soluble substances, active components, water and humectants may be incorporated through the addition of w/o and o/w emulsifiers.

Nonionic emulsifiers are preferred for the purposes of the invention. Nonionic emulsifiers are distinguished by their dermatological compatibility and mildness and by their ecotoxicologically favorable properties. Compositions with an improved sensory profile are obtained by using a combination of nonionic w/o and o/w emulsifiers. The compositions according to the invention contain the emulsifier(s) in a quantity of 0 to 20% by weight, preferably 0.1 to 10% by weight and more particularly 0.1 to 10% by weight, based on the total weight of the composition.

Nonionic Emulsifiers

The group of nonionic emulsifiers includes, for example,
(1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;
(2) $C_{12/18}$ fatty acid monoesters and diesters of addition products of 1 to 50 mol ethylene oxide onto glycerol;
(3) sorbitan mono- and diesters of saturated and unsaturated fatty acids containing 6 to 22 carbon atoms and ethylene oxide addition products thereof;
(4) alkyl mono- and oligoglycosides containing 8 to 22 carbon atoms in the alkyl group and ethoxylated analogs thereof;
(5) addition products of 7 to 60 mol ethylene oxide onto castor oil and/or hydrogenated castor oil;
(6) polyol esters and, in particular, polyglycerol esters such as, for example, polyol poly-12-hydroxystearates, polyglycerol polyricinoleate, polyglycerol diisostearate or polyglycerol dimerate. Mixtures of compounds from several of these classes are also suitable;
(7) addition products of 2 to 15 mol ethylene oxide onto castor oil and/or hydrogenated castor oil;
(8) partial esters based on linear or branched, unsaturated or saturated $C_{6-22}$ fatty acids, ricinoleic acid and 12-hydroxystearic acid and polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) or mixed esters, such as glyceryl stearate citrate and glyceryl stearate lactate for example;
(9) polysiloxane/polyalkyl/polyether copolymers and corresponding derivatives;
(10) mixed esters of pentaerythritol, fatty acids, citric acid and fatty alcohol and/or mixed esters of $C_{6-22}$ fatty acids, methyl glucose and polyols, preferably glycerol or polyglycerol.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. These emulsifiers are w/o or o/w emulsifiers, depending on the degree of ethoxylation. $C_{12/18}$ fatty acid monoesters and diesters of addition products of ethylene oxide onto glycerol are known as lipid layer enhancers for cosmetic preparations.

According to the invention, particularly suitable and mild emulsifiers are the polyol poly-12-hydroxystearates and mixtures thereof marketed by Cognis GmbH under the name of "Dehymuls® PGPH" (w/o emulsifier) or "Eumulgin® VL 75" (mixture with Coco Glucosides in a ratio by weight of 1:1, o/w emulsifier) or "Dehymuls® SBL" (w/o emulsifier), cf. in particular EP 0 766 661 B1. The polyol component of these emulsifiers may be derived from substances which contain at least two, preferably 3 to 12 and more particularly 3 to 8 hydroxyl groups and 2 to 12 carbon atoms.

In principle, suitable lipophilic w/o emulsifiers are emulsifiers with an HLB value of 1 to 8 which are listed in numerous Tables and are well-known to the expert. Some of these emulsifiers are listed, for example, in Kirk-Othmer, "Encyclopedia of Chemical Technology", 3rd Edition, 1979, Vol. 8, page 913. The HLB value for ethoxylated products may also be calculated by the following formula: HLB=(100−L): 5, where L is the percentage by weight of lipophilic groups, i.e. fatty alkyl or fatty acyl groups, in percent by weight in the ethylene oxide adducts.

Of particular advantage from the group of w/o emulsifiers are partial esters of polyols, more particularly $C_{4-6}$ polyols, such as for example partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

In cases where water-soluble active components and/or small quantities of water are incorporated, it can also be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example 10-20 ethylene oxide units for o/w emulsifiers and 2040 ethylene oxide units for so-called solubilizers. Particularly advantageous o/w emulsifiers for the purposes of the invention are Ceteareth-12 and PEG-20 stearate. Particularly suitable solubilizers are Eumulgin® HRE 40 (INCI name: PEG40 hydrogenated castor oil), Eumulgin® HRE 60 (INGI name: PEG-60 hydrogenated castor oil), Eumulgin® L (INCI name: PPG-1-PEG-9 laurylglycolether) and Eumulgin® SML 20 (INCI name: polysorbat-20).

Nonionic emulsifiers from the group of alkyl oligoglycosides are particularly compatible with the skin and are therefore particularly suitable as o/w emulsifiers. $C_{8-22}$ alkyl mono- and oligoglycosides, their production and their use are known from the prior art. They are produced in particular by reacting glucose or oligosaccharides with primary alcohols containing 8 to 22 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based. Products available under the name of Plantacare® contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the name of Emulgade® PL 68150 by Cognis GmbH, which is a 1:1 mixture of alkyl polyglucosides and fatty alcohols, is preferred for the purposes of the invention. According to the invention, the mixture of lauryl glucoside, polyglyceryl-2-dipolyhydroxystearate, glycerol and water which is marketed as Eumulgin® VL 75 may also be used with advantage in accordance with the invention.

A particularly preferred embodiment of the composition according to the invention contains (a) 1 to 50% by weight of at least one oil or wax component selected from $C_{14-30}$ dialkyl(ene) ethers, $C_{14-30}$ dialkyl (ene) carbonate, $C_{9-34}$ dicarboxylic acids, $C_{12-30}$ hydroxyfatty alcohols and a mixture of these substances,
(b) 0.1 to 5% by weight of at least one active component,
(c) 1 to 10% by weight of at least one oil,
(d) 0.1 to 10% by weight of at least one emulsifier,
(e) 5 to 90% by weight of one or more other wax components not listed in (a), and
(f) 0 to 5% by weight of water.

Other Surfactants/Emulsifiers (Optional)

The compositions may additionally contain zwitterionic, amphoteric, cationic and anionic surfactants according to the application envisaged for the wipes and tissues.

Zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the INCI name of Cocamidopropyl Betaine is a particularly preferred zwitterionic surfactant.

Ampholytic surfactants are also suitable, particularly as co-surfactants. Ampholytic surfactants are surface-active compounds which, in addition to a $C_{8/18}$ alkyl or acyl group, contain at least one free amino group and at least one $—COOH$ or $—SO_3H$ group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Anionic surfactants are characterized by a water-solubilizing anionic group, such as for example a carboxylate, sulfate, sulfonate or phosphate group, and a lipophilic residue. Dermatologically compatible anionic surfactants are known to the expert in large numbers from relevant manuals and are commercially available. More particularly, they are alkyl sulfates in the form of their alkali metal, ammonium or alkanolammonium salts, alkyl ether sulfates, alkyl ether carboxylates, acyl isethionates, acyl sarcosinates, acyl taurines with linear $C_{12-18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions according to the invention with particular softness. They are known substances which are prepared by the relevant methods of organic chemistry. Other cationic surfactants suitable for use in accordance with the invention are the quaternized protein hydrolyzates.

Other Auxiliaries and Additives

The compositions according to the invention may contain a number of other auxiliaries and additives depending on their intended application, including for example superfatting agents, thickeners, polymers, other waxes, biogenic agents, deodorants, film formers, UV protection factors, antioxidants, hydrotropes, preservatives, insect repellents, self-tanning agents, solubilizers, perfume oils, dyes and the like.

Superfatting agents may be selected from such substances as, for example, lanolin and lecithin and also polyethoxylated or acylated lanolin and -lecithin derivatives, polyol fatty acid esters, monoglycerides and fatty acid alkanolamides.

Suitable thickeners include, for example, Aerosil® hydrophilic silicas, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Inorganic and organic powders contribute towards further improving the sensory properties of the product. Accordingly, a preferred embodiment of the composition according to the invention additionally contains at least one powder. This powder is present in the compositions according to the invention in a quantity of typically 0.5 to 10% by weight, preferably 1 to 8% by weight and more particularly 1 to 5% by weight, based on the composition as a whole. Powders in the context of the invention are generally understood to be an accumulation of solid particles with a particle size below 100 nm which is used as a medicinal or cosmetic preparation for local application to healthy or diseased skin (source: CD Römpp Chemie Lexikon—Version 1.0, Stuttgart/New York: Georg Thieme Verlag 1995).

Powders are divided according to their consistency into flowable powders, loose powders (scattering powders), compacted powders (compacts), powder creams and powders in aerosol form. All these forms may be incorporated in the preparations according to the invention. The main constituent of the powders may be fine, single or mixed, absorbent, opaque, nontoxic materials which adhere to the skin, such as silicon dioxide, precipitated chalk, magnesium carbonate, kaolin, talcum, zinc oxide, titanium dioxide, strontium carbonate and sulfate, calcium sulfate, bismuth salts, stearates of Mg, Zn, Ti, Ca and Al, also rice, corn and wheat starch, lycopodium, iris root and ground silk. Aluminium Starch Octenylsuccinate (Dry Flo® PC), talcum, baby powder and silica gel are particularly preferred for the purposes of the invention.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, lauryldimonium hydroxypropyl hydrolyzed collagen (Lamequat® from L/Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®/Sandoz), copolymers of acrylic acid with dimethyl diallyl ammonium chloride (Merquat®550/Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 from Cela-nese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

For application to tissues and wipes designed to reduce body odor and perspiration, deodorizers and antiperspirants are additionally incorporated in the compositions according to the invention. Suitable deodorizers are, for example, antiperspirants, such as aluminium chlorhydrates, aluminium/zirconium chlorhydrates and zinc salts. These antiperspirants probably act by partially blocking the sweat glands through the precipitation of proteins and/or polysaccharides. Besides the chlorhydrates, aluminium hydroxylactates and acidic aluminium/zirconium salts may also be used. For example, an aluminium chlorhydrate which corresponds to the formula $[Al_2(OH)_5Cl].2.5H_2O$ and which is particularly preferred for the purposes of the invention is commercially available under the name of Locron® from Clariant GmbH. The aluminium/zirconium tetrachlorohydrex/glycine complexes marketed, for example, by Reheis under the name of Rezal® 36G are also preferably used in accordance with the invention.

Other suitable deodorizers are esterase inhibitors, preferably trialkyl citrates, such as trimethyl citrate, tripropyl citrate, triisopropyl citrate, tributyl citrate and, in particular, triethyl citrate (Hydagen® C.A.T., from Cognis GmbH), which inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates such as, for example, lanosterol, cholesterol, campesterol, stigmasterol and sitosterol sulfate or phosphate, dicarboxylic acids and esters thereof for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester.

Antibacterial agents which influence the germ flora and destroy or inhibit the growth of perspiration-decomposing bacteria, may also be present in the emulsions. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

If the composition according to the invention is applied to sun protection wipes, UV protection factors are additionally incorporated. UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble.

The following are examples of oil-soluble UV-B filtering substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, and 2-cyano-3,3-phenylcinnamic acid-2-ethylhexyl ester (octocrylene);

esters of salicylic acid, preferably salicylic acid-2-ethylhexyl ester, salicylic acid-4-isopropylbenzyl ester, salicylic acid homomethyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and octyl triazone;

propane-1,3-diones such as, for example, 1-(4-tert.butylphenyl)-3-(4'-methoxyphenyl)-propane-1,3-dione;

ketotricyclo(5.2.1.0)decane derivatives.

Suitable water-soluble UV filters are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and makeup. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments, for example micronized zinc oxide, are preferably used in sun protection products.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to µmole/kg). Other examples include (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin. Still other examples include ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxid-dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Some of these compounds were mentioned above among the humectants. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine;

dialcoholamines, such as diethaolamine or 2-aminopropane-1,3-diol.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

A suitable self-tanning agent is dihydroxyacetone.

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used.

Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal.

Examples of suitable ketones include the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance.

Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, boisambrene forte, ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, vertofix coeur, iso-E-super, fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes. The dyes may be oil-soluble or water-soluble and are normally used in concentrations of 0.001 to 0.1% by weight, based on the mixture as a whole. In a preferred embodiment, the compositions according to the invention contain at least one oil-soluble dye. The addition of the dye has the advantage that the stability of the composition applied to the wipes is easy to visualize. For example, in cases where the wipes are aftertreated with aqueous/surfactant-containing solutions, it is thus possible to see whether the wax and water phases gradually become mixed in the event of prolonged storage. Suitable oil-soluble dyes are, for example, C.I. 47000, C.I. 67565, C.I. 26100, C.I. 60725, C.I. 12150, C.I. 75810, C.I. 75300.

The present invention also relates to a process for treating human skin involving contacting the skin with an article used for personal hygiene, said article comprising a paper substrate coated with a composition having a melting point above about 25° C., which contains a primary wax or oil component selected from the group consisting of a $C_{14-30}$-dialkyl carbonate, a $C_{14-30}$-dialkylene carbonate, and mixtures thereof; up to about 10% by weight of water; and optionally one or more members selected from the group consisting of a secondary wax or oil component selected from the group consisting of a dialky(ene) ether, a dialkylene ether, a dicarboxylic acid, a hydroxy fatty alcohol, and mixtures of two or more thereof; a wax-like lipid component other than a primary and secondary wax or oil component; an oil component other than a primary and secondary wax or oil component; an emulsifier; an physiologically-active ingredient; and one or more auxiliaries and/or additives. A preferred process according to the invention involves the primary wax or oil component being present in the composition in an amount of from about 1-to-50%, by weight, the water is present in an amount of up to about 5%, by weight, and wherein the composition further contains from about 0.1-to-5%, by weight, of a physiologically-active ingredient; from about 1-to-about 10%, by weight, of an oil component other than a primary wax or oil component; from about 0.1-to-10%, by weight, of an emulsifier; and from about 5-to-90%, by weight, of a wax component other than the primary wax or oil component, all weights being based on the total weight of the composition.

FORMULATION EXAMPLES

To assess its performance properties, the composition according to the invention was stability-tested and its sensory properties were evaluated in a volunteer test. Commercially available wipes (substrate) weighing 60 g/m² were coated with compositions 1 to 19 according to the invention and with comparison preparations C1 and C2 in quantities of 0.3 g per gram substrate 195 g/m². The wipes coated with the compositions according to the invention are superior to known compositions in regard to sensory properties and storage stability. The storage stability of the wipes was evaluated after 12 weeks' storage after the compositions had been applied to the wipes together with a dye (phase 1) and the wipes had been aftertreated with an aqueous/surfactant-containing solution (phase 2). Any mixing of the phases is easy to see from the dye.

The quantities mentioned in the following Examples are based on % by weight of the commercially available substances in the composition as a whole, unless otherwise indicated. Examples 1 to 25 are formulations corresponding to the invention; C1 and C2 are Comparison Examples.

TABLE 1

| Composition | evaluation | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Lanette ® 14 | 58.99 | 47.99 | 47.99 | 47.99 | | | | | | | | 20.0 |
| Novata ® B | | | | | 64.99 | 54.99 | 49.99 | 39.99 | 58.99 | 30 | 19.99 | 10 |
| Lanette ® 16 | | | | | 32 | 33 | | | | | | |
| Lanette ® O | | | | | | | 20 | 20 | | 1 | 30 | |
| Lanette ® 18 | 23 | 25 | 20 | 25 | | | | | | | | |
| Cegesoft ® HF 52 | | | | | | | 5 | 10 | | 20 | | 20 |
| Cegesoft ® GPO | | | | | | | | | | 5 | | |
| Cegesoft ® PS 6 | | | | | | | 3 | 10 | | | 10 | |
| Eumulgin ® VL 75 | | 2 | 2 | 2 | | | | | | | 10 | 10 |

TABLE 1-continued

| Composition | evaluation | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Eumulgin ® B1 | | | | | | 3 | 2 | 1 | | 15 | 5 | |
| Cutina ® MD | | | | | | 4 | 2 | 1 | 25 | 20 | 10 | 20 |
| Monomuls ® 90-L 12 | | | | | | | | | 14 | | | |
| Cithrol ® 10 MS | 15 | 14 | 14 | 10 | | | 10 | | | | | 5 |
| Distearyl carbonate | 2 | 5 | 5 | | | 2 | | 5 | 1 | | 5 | 2 |
| Distearyl ether | | | | 7 | 1 | | 2 | 5 | | 5 | | |
| Tocopherol | 1 | 1 | 1 | 2 | 1 | 1 | | 1 | 1 | 1 | | |
| Tospearl ® 145 A | | | 5 | | | | | 2 | | | 5 | |
| Dye DC Green | 0.01 | 0.01 | 0.01 | 0.01 | 0.01 | 0.01 | 0.01 | 0.01 | 0.01 | | 0.01 | 0.01 |
| Zinc stearate | | | | 1 | | | | | 1 | | 2 | |
| Panthenol | | | | 1 | | | 1 | | | 1 | | 3 |
| Bisabolol | | | | | 1 | | | | | | | |
| Water | | | | | | to 100 | | | | | | |

The penetration values as measured with a penetrometer (Petrotester PNR 10, microcone, 5 secs., 20° C.) are 0.54 mm-2.43 mm.

TABLE 2

| Composition | evaluation | | | | | | | | |
|---|---|---|---|---|---|---|---|---|---|
| | 13 | 14 | 15 | 16 | 17 | 18 | 19 | C1 | C2 |
| Lanette ® 14 | 47.99 | | 47.99 | | | | | 75 | |
| Novata ® B | | 47.99 | | 47.99 | 40.0 | 55.99 | 50.99 | | 80 |
| Lanette ® 16 | | | | | 50.0 | | | | 10 |
| Lanette ® O | | | | | | | | 10 | 10 |
| Lanette ® 18 | 25 | 16 | 20 | 20 | | | | 15 | |
| Cegesoft ® HF 52 | | | | | | | | | |
| Cegesoft ® GPO | | | | | | | | | |
| Cegesoft ® PS 6 | | | | | | | | | |
| Emulgade ® PL 68/50 | | 2 | 2 | | 1.0 | | | | |
| Eumulgin ® VL 75 | 2 | | | 2 | | | | | |
| Eumulgin ® B1 | | | | | | | | | |
| Cutina ® MD | | 16 | | | | 20 | 25 | | |
| Monomuls ® 90-L 12 | | | | | | 15 | 15 | | |
| Cithrol ® 10 MS | 14 | | 16 | 12 | | | | | |
| Hexadecane-1,2-diol | 5 | 4 | 5 | | | | | | |
| Distearyl carbonate | | | | 5 | 2 | 5 | | | |
| Distearyl ether | | 6 | | | 2 | | 5 | | |
| Azelaic acid | | | | | 3 | | | | |
| Tocopherol | 1 | | | | 1 | | | | |
| Dow Corning ® DC 245 | | | | 3 | | | | | |
| Talcum | | | | | | 2 | 2 | | |
| Dry Flo ® PC | | | | | | | 2 | | |
| Tospearl ® 145 A | | | | 5 | | | | | |
| Dye C.I. 45430 | 0.01 | 0.01 | 0.01 | 0.01 | 0.01 | 0.01 | 0.01 | | |
| Timiron ® Splendid Gold | | | | | | | 2 | | |
| Water | | | | | to 100 | | | | |

The penetration values as measured with a penetrometer (Petrotester PNR 10, microcone, 5 secs., 20° C.) are 0.54 mm-2.43 mm.

TABLE 3

| Composition | evaluation | | | | | |
|---|---|---|---|---|---|---|
| | 20 | 21 | 22 | 23 | 24 | 25 |
| Lanette ® 14 | 55 | 24.988 | 19.76 | 24.988 | 19.9 | 19.9 |
| Novata ® B | | 25 | 20 | 25 | 20 | 20 |
| Lanette ® 16 | | | | | | |
| Lanette ® O | | | | | | |
| Lanette ® 18 | 25 | 15 | 20 | 15 | 20 | 20 |
| Eumulgin ® B1 | | | | | 2 | 2 |
| Cutina ® MD | | 5 | 10 | 5 | 10 | 10 |
| Monomuls ® 90-L 12 | | 15 | 10 | 15 | 10 | 8 |
| Cithrol ® 10 MS | 13.976 | | | | | |
| Hexadecane-1,2-diol | | 2 | | | | |

TABLE 3-continued

| Composition | evaluation | | | | | |
|---|---|---|---|---|---|---|
| | 20 | 21 | 22 | 23 | 24 | 25 |
| Distearyl carbonate | | | | | | |
| Distearyl ether | | 5 | 10 | 5 | 10 | 10 |
| Vitamin E Primaspheres ® | 3 | 5 | 10 | | | |
| Tocopherol | 1 | | | | | |
| Dipropylene glycol | | | | | | 2 |
| Vitamin A Primaspheres ® | | | | 5 | 8 | 8 |
| Dry Flo ® PC | | | | 5 | | |
| Dye DC Green | 0.015 | 0.015 | 0.009 | 0.012 | | |
| Dye DC Violett | 0.009 | 0.015 | 0.009 | | 0.1 | 0.1 |
| Water | | | to 100 | | | |

PRODUCT/TRADEMARK GUIDE

1) Cegesoft® GPO
   INCI: Palm (Elaeis Guineensis) oil
   Manufacturer: Cognis GmbH
2) Cegesoft® HF 52
   INCI: Hydrogenated Vegetable oil
   Manufacturer: Cognis GmbH
3) Cegesoft® PS 6
   INCI: Vegetable oil
   Manufacturer: Cognis GmbH
4) Cithrol® 10 MS
   INCI: PEG-20 stearate
   Manufacturer: Croda Surfactants Ltd.
5) Cutina® MD
   INCI: Glyceryl stearate
   Manufacturer: Cognis GmbH
6) Dow Corning DC® 245
   INCI: Cyclomethicone
   Manufacturer: Dow Corning
7) Dry Flo® PC
   INCI: Aluminum starch octenylsuccinate
   Manufacturer: National Starch
8) Emulgade® PL 68/50
   INCI: Cetearyl glucoside, cetearyl alcohol
   Manufacturer: Cognis GmbH
9) Eumulgin® B1
   INCI: Ceteareth-12
   Manufacturer: Cognis GmbH
10) Eumlugin® VL 75
    INCI: Lauryl glucoside, polyglyceryl-2 dipolyhydroxystearate, glycerin, aqua (Water); ca. 75% active substance in water
    Manufacturer: Cognis GmbH
11) Lanette® 14
    INCI: Myristyl alcohol
    Manufacturer: Cognis GmbH
12) Lanette® 16
    INCI: Cetyl alcohol
    Manufacturer: Cognis GmbH
13) Lanette® 18
    INCI: Stearyl alcohol
    Manufacturer: Cognis GmbH
14) Lanette® O
    INCI: Cetearyl alcohol
    Manufacturer: Cognis GmbH
15) Monomuls®90-L 12
    INCI: Glyceryl laurate
    Manufacturer: Cognis GmbH
16) Novata® B
    INCI: Cocoglycerides
    Manufacturer: Cognis GmbH
17) Vitamin E Primaspheres®
    INCI: Vitamin E
    Manufacturer: Primacare; Cognis Iberia
18) Vitamin A Primaspheres®
    INCI: Vitamin A
    Manufacturer: Primacare; Cognis Iberia
19) Timiron® Splendid Gold
    INCI: Titanium dioxide and mica and silica
    Manufacturer: Rona EM Industries, Inc. NY
20) Tospearl® 145 A
    INCI: Polymethylsilsesquioxane
    Manufacturer: Bayer GE Silicones
21) Tospearl® 145 A
    INCI: Polymethylsilsesquioxane
    Manufacturer: Bayer GE Silicones

What is claimed is:

1. A wax-based composition comprising:
   (a) from about 1% to about 20%, based on the weight of the composition, of one or more wax components selected from the group consisting of a C14-30 dialkyl carbonate, a C14-30 dialkylene carbonate, and mixtures thereof, having a melting point or mixture melting point greater than about 25° C.; and
   (b) up to about 10%, by weight, of water,
   wherein said composition is wax-based, with a melting point of the composition of above 25° C.

2. The wax-based composition of claim 1 further comprising one or more wax or oil components selected from the group consisting of a dialkyl ether, a dialkylene ether, a dicarboxylic acid, an hydroxyfatty alcohol, and mixtures of two or more thereof.

3. The wax-based composition of claim 1 further comprising a wax-like lipid component other than a wax component of claim 1 or a wax or an oil component selected from the group consisting of a dialkyl ether, a dialkylene ether, a dicarboxylic acid, and an hydroxyfatty alcohol.

4. The wax-based composition of claim 1, wherein component (a) is present in about 1% to about 10%, based on the weight of the composition.

5. The wax-based composition of claim 1 wherein component (a) comprises saturated unbranched C16-22 dialkyl carbonates.

6. The wax-based composition of claim 5 wherein component (a) comprises distearyl carbonate.

* * * * *